(12) United States Patent
Farangis et al.

(10) Patent No.: US 8,491,766 B2
(45) Date of Patent: Jul. 23, 2013

(54) GAS SENSOR FOR DETERMINING HYDROGEN OR HYDROGEN COMPOUNDS

(75) Inventors: Baker Farangis, Giessen (DE); Bruno K. Meyer, Grossen-Linden (DE); Hans-Peter Jorde, Fernwald (DE); Jennifer Stiebich, Reiskirchen (DE)

(73) Assignee: Justus-Liebig-Universitat Giessen, Giessen (DE)

( * ) Notice: Subject to any disclaimer, the term of this patent is extended or adjusted under 35 U.S.C. 154(b) by 733 days.

(21) Appl. No.: 12/085,567

(22) PCT Filed: Nov. 29, 2006

(86) PCT No.: PCT/DE2006/002109
§ 371 (c)(1), (2), (4) Date: May 28, 2008

(87) PCT Pub. No.: WO2007/062629
PCT Pub. Date: Jun. 7, 2007

(65) Prior Publication Data
US 2009/0283421 A1 Nov. 19, 2009

(30) Foreign Application Priority Data
Nov. 29, 2005 (DE) .......................... 10 2005 057 214

(51) Int. Cl.
*G01N 27/407* (2006.01)
(52) U.S. Cl.
USPC ........................................................ 204/424
(58) Field of Classification Search
USPC .................. 204/410, 411, 421–429; 73/23.2, 73/31.05, 31.06; 436/144, 147; 422/83, 88
See application file for complete search history.

(56) References Cited

U.S. PATENT DOCUMENTS

| 4,953,387 A * | 9/1990 | Johnson et al. ............... 73/25.03 |
| 5,591,321 A | 1/1997 | Pyke |
| 7,370,511 B1 * | 5/2008 | Chen et al. ..................... 73/23.2 |
| 2003/0153088 A1 * | 8/2003 | DiMeo et al. ................. 436/113 |
| 2004/0223884 A1 * | 11/2004 | Chen et al. ....................... 422/88 |
| 2005/0072673 A1 | 4/2005 | Fukuda |

FOREIGN PATENT DOCUMENTS

| DE | 101 45 719 | | 4/2003 |
| DE | 102 61 299 | A1 | 7/2003 |
| DE | 101 96 864 | | 11/2003 |

OTHER PUBLICATIONS

Richardson, T.J. et al., "Mixed metal films with switchable optical properties", *Applied Physics Letters*, vol. 80 (8), 2002, pp. 1349-1351.
Yoshimura, Kazuki et al., "Room-temperature hydrogen sensor based on pd-capped Mg2Ni thin film", *Japanese Journal of Applied Physics*, vol. 43 (4b), 2004, pp. L507-L509.
Bodzenta, Jerzy et al., "Thin palladium film as a sensor of hydrogen gas dissolved in transformer oil", *Sensors and Actuators*, vol. 87, 2002, pp. 82-87.
Farangis, B., "Structural and electronic properties of magnesium-3D transition metal switchable mirrors", Solid State Ionics vol. 165, 2003, pp. 309-314.

* cited by examiner

*Primary Examiner* — Luan Van
*Assistant Examiner* — Gurpreet Kaur
(74) *Attorney, Agent, or Firm* — Clark & Brody

(57) ABSTRACT

The invention at hand concerns a novel class of gas sensors, in particular for hydrogen or hydrogen-containing fluids (gases or liquids), such as hydrocarbons, hydrogen sulphides or more complex gas mixtures or gas compositions which contain hydrogen or hydrogen compounds.

6 Claims, 3 Drawing Sheets

GAS SENSOR FOR DETERMINING HYDROGEN OR HYDROGEN COMPOUNDS

DESCRIPTION AND STATE OF THE ART

Figure 1:
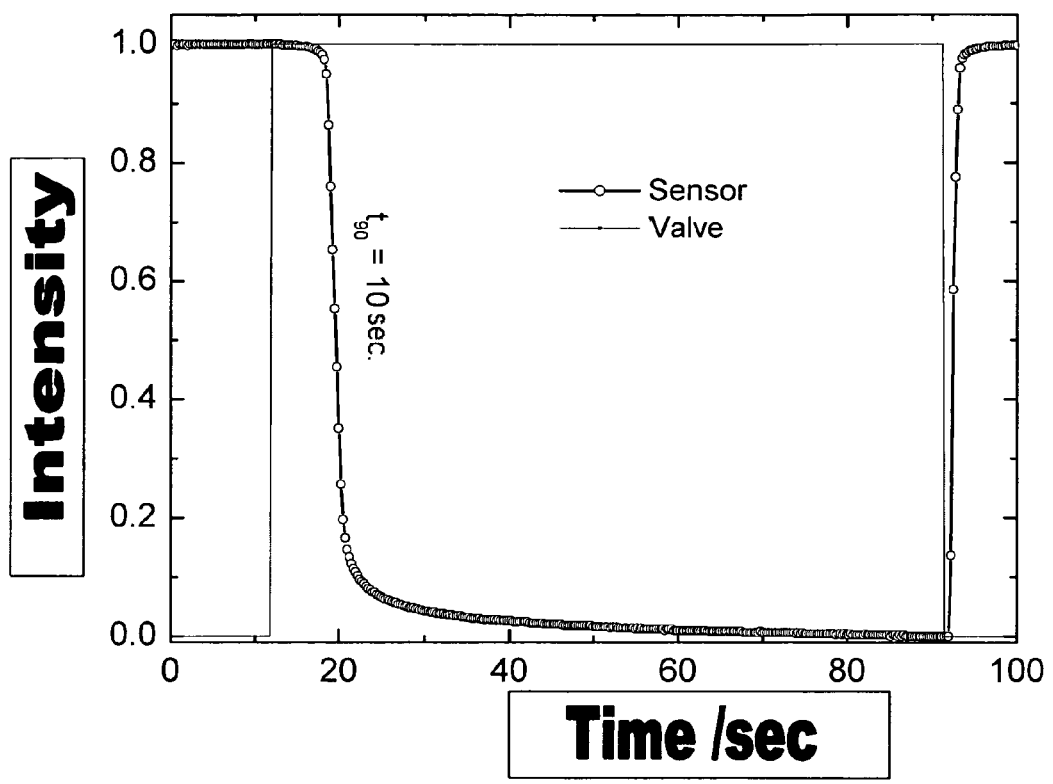

The invention at hand concerns a novel class of gas sensors, in particular for hydrogen or hydrogen containing fluids (gases or liquids), such as hydrocarbons, hydrogen sulphides or more complex gas mixtures or gas compositions which contain hydrogen or hydrogen compounds.

Such sensors find application in many areas, e.g. the industry and there for instance in the chemical industry or in the production of semiconductors.

Already a wide range of gas sensors, also for the measurement of gases which contain hydrogen, are known by the state of the art. DE 102 61 299, e.g., shows known gas sensors which use for the detection of flammable gases solid electrolytes (as, e.g., zirconium oxide) conducting oxide ions.

Other gas sensors use—as, e.g., in U.S. Pat. No. 5,591,321—metal-insulator-semiconductor-diodes (MIS-Sensors) for the detection of gases.

As well known are those gas sensors which use the solid state electrolysis as principle of measurement.

Other gas sensors—such as shown, e.g., in DE 101 45 719—use optical examination processes for the detection of gases.

While the latter possess the advantage that no danger is caused by the measurement through electrical currents (risk of sparks) or high temperatures (solid state electrolysis at, e.g., 600° C.) which are required within the highly explosive gas environment, also the last mentioned sensor type comprises the disadvantage that the measurements are relatively complex. For that purpose, very complex devices are required.

All aforementioned sensor types comprise also the disadvantage that the detection of gas either is carried out through the application of tensions or electric currents, or, however, is realised exclusively through optical detection.

A simple and reliable sensor, which is cost-efficient both when in operation and in production and is suitable for being used—without any constructional modifications of the sensor as such—for optical or electrical "reading", is until now completely unknown.

AIM OF THE INVENTION

It is thus the aim of the invention to provide a new type of gas sensors which avoid the aforementioned disadvantages in the state of the art.

Furthermore, it is the aim of the current invention to provide a method for the measurement of hydrogen-containing gases.

Surprisingly it has been found that a combination of magnesium, in particular also in the cost-efficiently producible amorphous, but also the microcrystalline or polycrystalline form, combined with means to activate, cleave or dissociate (i.e. transfer of one hydrogen in ionic or atomic form) which are realised and arranged in such a way, that the activated or cleaved or dissociated hydrogen parts find access to the magnesium, achieves the aforementioned first aim.

Thereby, the magnesium is suitable for being used alone or in combination with Ni, also in the fixed combination as $Mg_2Ni$ or in free combination of the parts of Mg and Ni, or also in combination with Al and further substances of the group Li, Be, Na, Ti, V, Cr, Mn, Fe, Co, Ni, Zr, Nb, Mo, Tc, Ru, Rh, Pd, Ag, Cd, Hf, Ta, W, Re, Os, Ir, Pt, Au, Hg, Si, K, Ca, Ga, Ge, As.

For the development of an independent sensor, it was found that a basic sensor should comprise the following composition:
a) substrate,
b) functional layer or functional area
c) means of activation or cleavage of hydrogen

EMBODIMENTS

In a particularly preferred embodiment, which is suitable for being read not only optically but also electronically, the substrate consists of a transparent material, e.g. glass or plastic or polymers or semiconductors.
In this embodiment, no means of electronic connection are necessary.

The functional layer or the functional area are suitable for, in the optical or in the electrical embodiment, comprising amorphous, microcrystalline or polycrystalline Mg, or $Mg_2Ni$, or MgAl or $MgAl_{(1-x)}Ni_x$ or in the form of Mg with Al and further free combinations of elements from the following group: Li, Be, Na, Ti, V, Cr, Mn, Fe, Co, Ni, Zr, Nb, Mo, Tc, Ru, Rh, Pd, Ag, Cd, Hf, Ta, W, Re, Os, Ir, Pt, Au, Hg, Si, K, Ca, Ga, Ge, As.

The means of activation or cleavage or dissociation (in the above sense) of hydrogen are suitable for being realised—provided that the sensor is realised as a layer system—in the form of a top layer from Pd or Pt or other hydrogen activating or hydrogen cleaving or hydrogen dissociating layers which are arranged above the functional layer. These means have to be realised in such a way that the activated or cleaved or dissociated hydrogen can still interact with the active layer in such a way that a measurement of the product of the hydrogen activation or cleavage or dissociation thereof can take place.

A particularly preferred embodiment, which comprises a particularly long "service life" (i.e. the sensor is suitable—in comparison to other sensors—without interfering with the measurement function, for being exposed particularly long to oxygen containing or other oxidising environments), comprises apart from magnesium also aluminium as a component of the functional layer. Apart from aluminium, also other catching means for oxidising substances can be used, e.g. vanadium or Li or Na are suitable, provided that these are able to bind oxygen or oxygen compounds or other oxidants or to absorb and therewith prevent a "poisoning" (e.g. "oxygen poisoning") of the actually sensitive magnesium parts of the sensor or at least delay this poisoning.

The examinations in which Mg and/or Al was or were used as part of the functional layer or functional areas, comprised—compared with sensors with Mg and Ni in amorphous, microcrystalline or partly polycrystalline form in the functional layer—a further advantage, namely that the response times are considerably shorter in embodiments with aluminium. In principle, also further embodiments comprising apart from Mg and Al such elements which form hydrides such as Li, Be, Na, Ti, V, Cr, Mn, Fe, Co, Ni, Zr, Nb, Mo, Tc, Ru, Rh, Pd, Ag, Cd, Hf, Ta, W, Re, Os, Ir, Pt, Au, Hg, Si, K, Ca, Ga, Ge, As comprise the aforementioned advantages of the shorter response time or the longer service life.

In the electrical embodiment are, between the substrate and the functional layer or the functional area, electrodes or conductors arranged which enable the measurement of an electrical tension or its variation through the functional layer or the functional areas. In the purely electrical embodiment also the substrate is suitable for being made of—for light—nontransparent material.

In the combined optical and electrical embodiment, the electrodes or the correspondingly usable conductors should be realised or arranged in such a way that—in the case of optical reading—the light used can fall on at least a part of the functional layer. Thus, the conductor paths or the conducting surfaces or electrodes have either to be transparent for the respective light or are not allowed to cover the whole surface of the active layer or active areas. In case the hydrogen activating, cleaving or dissociating layer is realised to be transparent for the respective light, the conductor paths or the conducting surfaces can also be realised to be non-transparent for the respective light. The same applies for the substrate.

A special embodiment of the purely optical embodiment comprises, in the case of glass as substrate or comparable substrates, an additional nucleation layer or adhesion layer for the functional layer or the functional areas. For that purpose, $TiO_x$ or $SiO_x$ come into question. This nucleation layer is also suitable for being used in the purely electrical embodiment.

In the following, further embodiments are shown.

Figure 2:
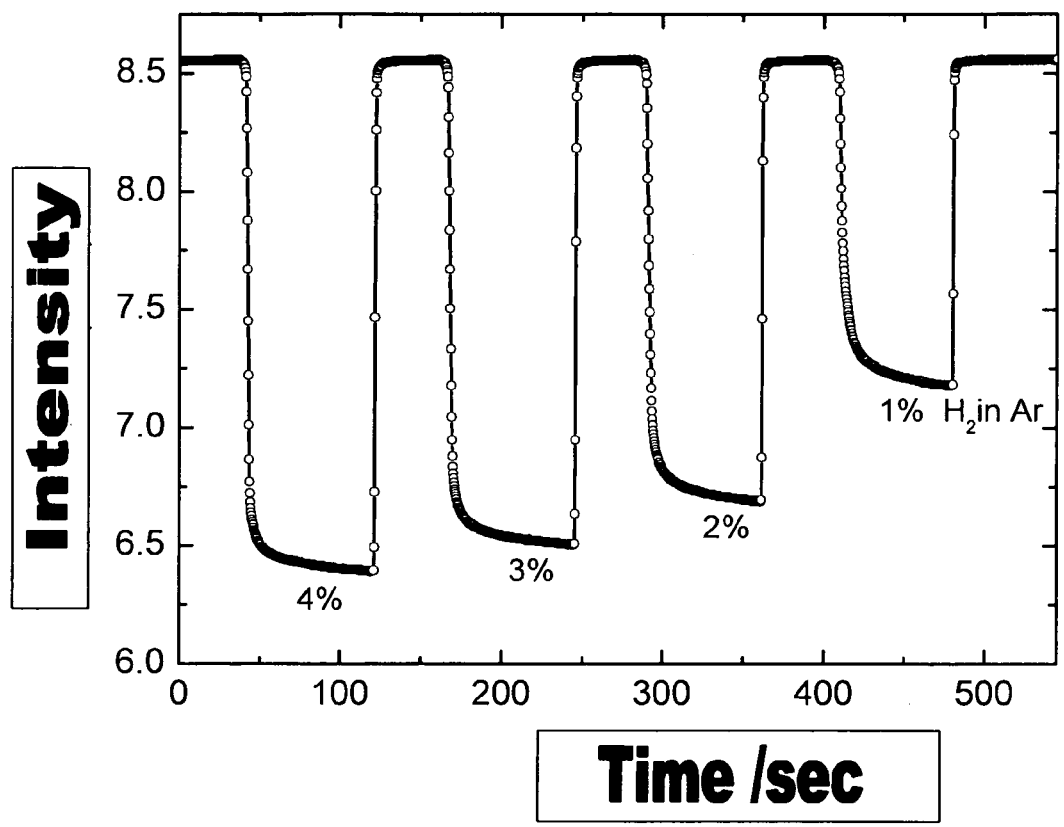
Figure 3:
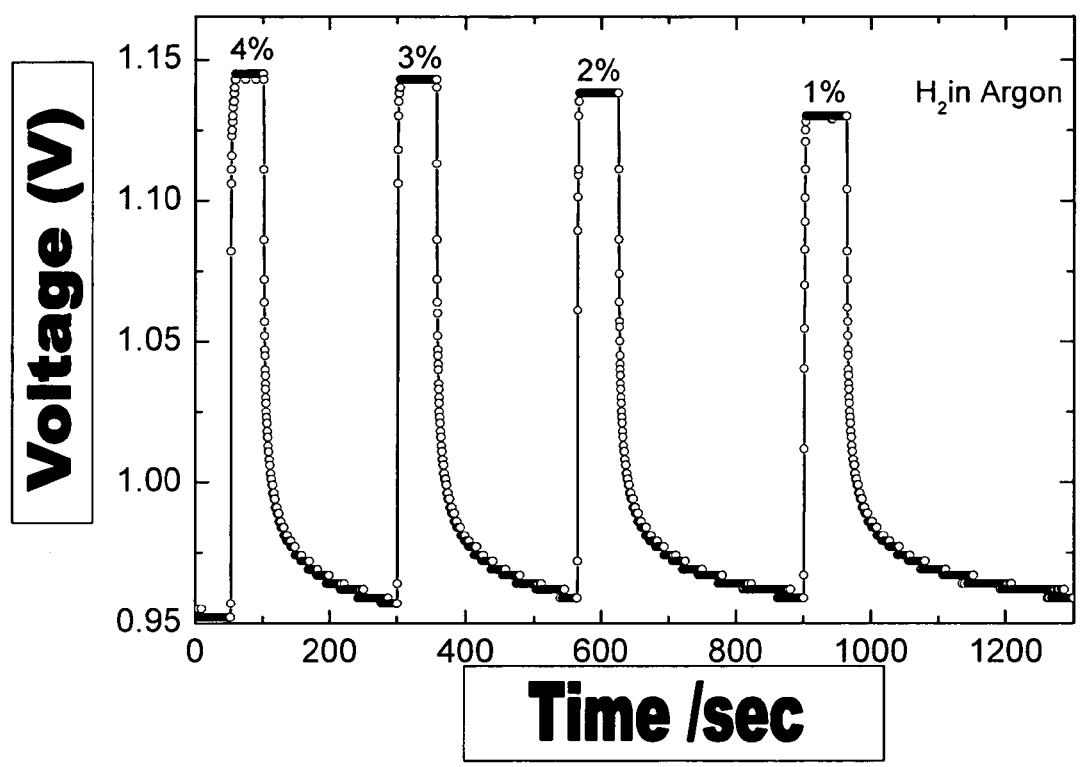

The following figures show:

FIG. 1 the optical response of the gas sensor according to the present invention in the optical embodiment after the inlet (opening of the valve) of hydrogen FIG. 2 the optical response of a sensor according to FIG. 1 when varying hydrogen concentrations are added FIG. 3 the electrical responses i.e. changes in tension when varying hydrogen concentrations are added The aforementioned functional layers, particularly in pure amorphous, microcrystalline and/or partly polycrystalline realisation, which are deposited e.g. on glass substrates by means of sputter-methods or other thin-film deposition methods, are, upon interaction with hydrogen (metal hydrides), suitable for comprising both electrochrome as well as gasochrome characteristics.

By charging with hydrogen the electrical characteristics (resistance) vary or also the optical characteristics (highly reflective, non-transmitting in a transmitting, low reflective state). These characteristics are adjustable by the composition of the actual functional layer in a thickness of e.g. between 30-50 nm (magnesium-nickel-alloy) with a catalytic palladium-top layer e.g. between 7-10 nm. Thus, the transmitting state is practically independent of the wavelength. Changes in resistance or changes of optical characteristics and their timely response to the addition of hydrogen are suitable for being controlled through the composition (Mg vs Ni or Mg vs Al in free combination), layer thickness and other things. As a result, two different types of sensors are suitable for being realised.

To FIG. 1: Optical sensor

With this method the change of the optical characteristics, i.e. for instance the transmission change during the hydrogen absorption, is detected. A GaAs IR luminescence diode serves as light source in this embodiment and as detector e.g. a NPN silicon photo transistor, which measures the reflected intensity. The size of the probe was 6 mm×6 mm.

FIG. 1 shows a measurement with 4% hydrogen in argon at room temperature. The signal intensity before and after the hydrogen absorption remains stable and the absorption of the hydrogen occurs quickly, and attains 90% of the maximum value ($t_{90}$) within 10 seconds.

FIG. 2 shows the sensitivity of the sensor to different hydrogen concentrations from 1-4%, whereby the lowest detection limit was in the range of approx. 0.1%.

In addition, the invention concerns a novel method regarding the measurement of hydrogen or hydrogen-containing compounds such as e.g. hydrocarbons or hydrogen sulphides.

For that purpose, the gas to be measured, comprising hydrogen or hydrogen-containing compounds, is led to a gas sensor according to the current invention, wherein the detection of the hydrogen concentration or the concentration of the hydrogen-containing compounds takes place through the absorption or release of the aforementioned gases on or by Mg or MgNi or MgAl or $MgAl_{(1-x)}Ni_x$ or in form of a free combination of Mg with Al with one or several elements of the following group: Li, Be, Na, Ti, V, Cr, Mn, Fe, Co, Ni, Zr, Nb, Mo, Tc, Ru, Rh, Pd, Ag, Cd, Hf, Ta, W, Re, Os, Ir, Pt, Au, Hg, Si, K, Ca, Ga, Ge, As, respectively in amorphous and/or microcrystalline and/or partly polycrystalline form.

The novel measurement method occurs in a particularly advantageous manner as above, but with a modification consisting in the simultaneous or periodical or repeated provision within the gas flow to be measured or determined or within the environment to be measured of a catching means, during the absorption or/and release by the aforementioned substances, in order to avoid the poisoning of the Mg, such as Al and/or vanadium and/or Li and/or Na. Thereby the service life of the sensor is considerably increased.

The production of the novel sensor-class takes place as follows:

Optical embodiment: the functional layer can be deposited on a substrate layer out of common transparent material such as glass or plexiglass or non-transparent material.

For the production, the substrate is coated with the functional layer or the functional areas by one of the known thin-film deposition methods, e.g. through the sputtering technique, the chemical vapour deposition from gas phases (CVD, MOCVD) the sol-gel process, vaporisation, treatment by pyrolysis.

A modification of the method for the production of the optical embodiment and thus an advantageous embodiment, compared to the method specified here, results when first a nucleation layer is deposited to the substrate on to which the functional layer is deposited. As a nucleation layer, such are particularly suitable which comprise a similar structure and lattice constant, in particular at the deposition temperature of the functional layer.

For the production of the electrical embodiment according to known methods, such as thermal evaporation, sputtering technique, chemical vapour deposition from gas phases (CVD, MOCVD), the sol-gel process, vaporisation, treatment by pyrolysis, or through wet-chemical deposition or by electrolysis, first an electrical conducting layer, or a conducting layer, is suitable for being deposited on the substrate likewise by the known or the aforementioned thin-layer deposition methods. In the purely electrical embodiment, no adhesion or nucleation layer is required. Thus, the functional layer can be deposited directly on the electrically conducting layer or the electrodes or the electrical conductors by the known methods or the aforementioned thin-film deposition methods.

Subsequently, the hydrogen-activating or hydrogen-cleaving or hydrogen-dissociating layer has to be deposited on this—in all embodiments—(i.e. purely optical or purely electrical or combined, a sensor to be read optically or electrically) by the aforementioned methods or known thin-layer deposition methods.

LIST OF REFERENCE NUMERALS

1 Substrate
2 Functional layer or areas
3 Activating or cleaving layer
4 Electrodes or electrical conductor paths
5 Nucleation or adhesion layer

The invention claimed is:

1. A gas sensor for the determination of the concentration of cleaved or activated or dissociated hydrogen in gases or fluids, the gas sensor having a substrate, a functional layer or functional areas, and means of activation or cleavage of hydrogen; said substrate, said functional layer or areas, and said means of activation or cleavage of hydrogen forming a layer system;
   wherein the substrate consists of a transparent material which is glass or plastic or polymers or semiconductors and the functional layer is an amorphous, microcrystalline or polycrystalline and is based on Mg in combination with at least one further element of the group consisting of Al, V, Li, and Na;
   wherein the means of activation or cleavage of hydrogen comprises a top layer of Pd or Pt which is arranged above the functional layer or functional areas.

2. The gas sensor according to claim 1, wherein the functional layer or functional areas are MgAl or $MgAl_{(1-x)}Ni_x$.

3. The gas sensor according to claim 1, wherein the gas the sensor is optically or electrically read, wherein the optical reading is carried out through the modification of a reflection degree of the functional layer or functional areas and the electrical reading by means of a modification of resistance of the functional layer or functional areas.

4. The gas according to claim 3, wherein the electrically readable gas sensor comprises electrical conductors or contacts, wherein the resistance modification of the functional layer or the functional areas is readable.

5. The gas sensor according to claim 3, wherein the gas sensor in a electrical or optically readable form comprises a nucleation layer or adhesion layer within areas between the substrate and the functional layer or the functional areas.

6. The gas sensor of claim 5, wherein the nucleation layer or the adhesion layer are in the form of TiOx and SiOx.

* * * * *